US00PP22085P3

(12) United States Plant Patent
Boyle

(10) Patent No.: US PP22,085 P3
(45) Date of Patent: Aug. 16, 2011

(54) CACTACEAE PLANT NAMED 'GAIL GLAZIER'

(50) Latin Name: *Schlumbergera truncata*
Varietal Denomination: Gail Glazier

(75) Inventor: Thomas H. Boyle, Amherst, MA (US); Nancy Bandman-Boyle, legal representative, Hadley, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 12/590,246

(22) Filed: Nov. 3, 2009

(65) Prior Publication Data

US 2011/0107484 P1 May 5, 2011

(51) Int. Cl.
*A01H 5/00* (2006.01)

(52) U.S. Cl. ..... Plt./372

(58) Field of Classification Search ..... Plt./372
See application file for complete search history.

*Primary Examiner* — Annette Para

(74) *Attorney, Agent, or Firm* — James R. Cypher; Charles R. Cypher

(57) ABSTRACT

A plant variety of the Cactaceae family, *Schlumbergera truncata*, called 'Gail Glazier' having a predominantly white colored bloom characterized as R.H.S 155 D (white group). The new variety has a strong resistance to bud abscission, a strong propensity for buds to mature and flower, an erect growth habit, and an ability to branch easily with minimal pruning, contributing to a dense appearance.

4 Drawing Sheets

Latin name of genus and species of plant claimed: The new plant is a species of *Schlumbergera truncata.*

Variety denomination: The new plant's varietal denomination is 'Gail Glazier.'

BACKGROUND OF THE INVENTION

The present invention relates to a new and distinct variety of the Cactaceae family. The new variety is named *Schlumbergera truncata* 'Gail Glazier'. The inventor is Thomas H. Boyle, a citizen of the United States.

Many varieties of *Schlumbergera truncata* tend to bloom in the winter in the Northern Hemisphere. Because of their blooming time, there is a large market for these varieties during the Thanksgiving and Christmas seasons as a decorative plant. In fact, the common name for these plants is Christmas Cactus.

There are many commercially developed varieties of Christmas Cactus. Patented varieties include: ('Lavender Doll' (Cobia, U.S. Plant Pat. No. 3,690); 'Christmas Charm' (Cobia et al., U.S. Plant Pat. No. 4,196); 'Rudolph' (Higaki, U.S. Plant Pat. No. 6,234); 'Dasher' (Higaki, U.S. Plant Pat. No. 7,367); and Rudolph II (Martens, U.S. Plant Pat. No. 10,487).

For many varieties of the species, bud abscission is a problem: a large portion of the initial buds that form on the plant fall off before they reach full maturity. Furthermore, many cultivars possess the further undesirable characteristic that many of the buds that do set on the plant fail to mature and bloom. Preferred cultivars resist bud abscission, as well as produce buds that have a propensity to mature.

The present variety, 'Gail Glazier' was developed at the University of Massachusetts, Amherst, and is a hybrid obtained by cross pollinating flowers of the commercial variety 'Think Pink' with pollen collected from flowers of the commercial variety 'Eva'.

'Gail Glazier' is characterized by its flower color, large flowers, reflexed tepals, and large phylloclades. The flower tepals are predominantly white with a blush of pink at the base and margins of the tepals and the mouth of the tube has a pink ring.

'Gail Glazier' resists bud abscission, as well as produces buds that have a propensity to mature. The present variety sets many buds per phylloclade often 2 to 3, many of which reach full maturity and bloom, generally 1 to 2.

This present variety is also outstanding for its propensity to grow tall and upright without too much spreading, thus giving it a dense appearance.

Comparison Table

| | 'Gail Glazier' New Variety | 'Harmony' U.S. Plant Pat. No. 18,177 |
|---|---|---|
| Mature Flower Pigmentation Color in Tepals | Sepaloid Series: R.H.S. 145A (yellow-green group) Tube Laminating Series: R.H.S. 155D (white group) Tube Forming: R.H.S. 73D (red-purple group) | Tepals are predominantly R.H.S. 46B (red group) with the Perianth tube being R.H.S. 68 D (red-purple group) and the margins of the blades of the perianth tube being R.H.S. 46 B (red group) and the central portions of the blades just above the tube are R.H.S. 155 C (white group). |
| Bud Color | R.H.S. 145 B (yellow-green group) | R.H.S 74 B (red-purple grp.) |
| Color of mature phylloclade | R.H.S. 146 A (yellow-green group) | R.H.S. 147 A (yellow-green group) |
| Tube forming series of tepals base to tip dimension: 65 to 74 mm | Length: 45 mm to 60 mm. Width: 23 mm to 35 mm. | Length: 45 mm to 53 mm. Width: 25 mm to 35 mm. |
| Size of Flowers | Tube forming series of tepals base to tip | Tube forming series of tepals base to tip |

-continued

| Comparison Table | | |
|---|---|---|
| | dimension: 65 to 74 mm | dimension: 50 to 70 mm |
| | 'Prancer' U.S. Plant Pat. No. 15,051 | 'Maria' Unpatented commercial var. |
| Mature Flower Pigmentation Color in Tepals | All series of tepals are predominantly R.H.S.74A (red-purple group) | R.H.S. 45 C (red group) |
| Bud Color | R.H.S. 67 A (red-purple grp.) | R.H.S. 74 B (red-purple grp.) |
| Color of mature phylloclade | Portions exposed to light are R.H.S. 137 B (yellow-green group). Shaded portions are R.H.S. 144 B (yellow-green group) | |
| Tube forming series of tepals base to tip dimension: 65 to 74 mm | Length: 45 mm to 60 mm. Width: 16 mm to 26 mm. | |
| Size of Flowers | Tube forming series of tepals base to tip dimension: 50 to 60 mm | |

In addition, the new variety also possesses the additional commercially desirable characteristics of a strong propensity to branch with minimal pruning, also contributing to its dense appearance.

The inventor has asexually reproduced the new variety at a commercial nursery in Half Moon Bay, Calif. through three successive generations by cuttings, and has found that the combination of characteristics as herein disclosed remain firmly fixed.

BRIEF DESCRIPTION OF THE DRAWING

The accompanying drawings serve, by color photographic means, to illustrate the new plant variety. The colors are represented as truly as possible using conventional photographic procedures.

DETAILED DESCRIPTION OF THE NEW VARIETY

Figure 1:
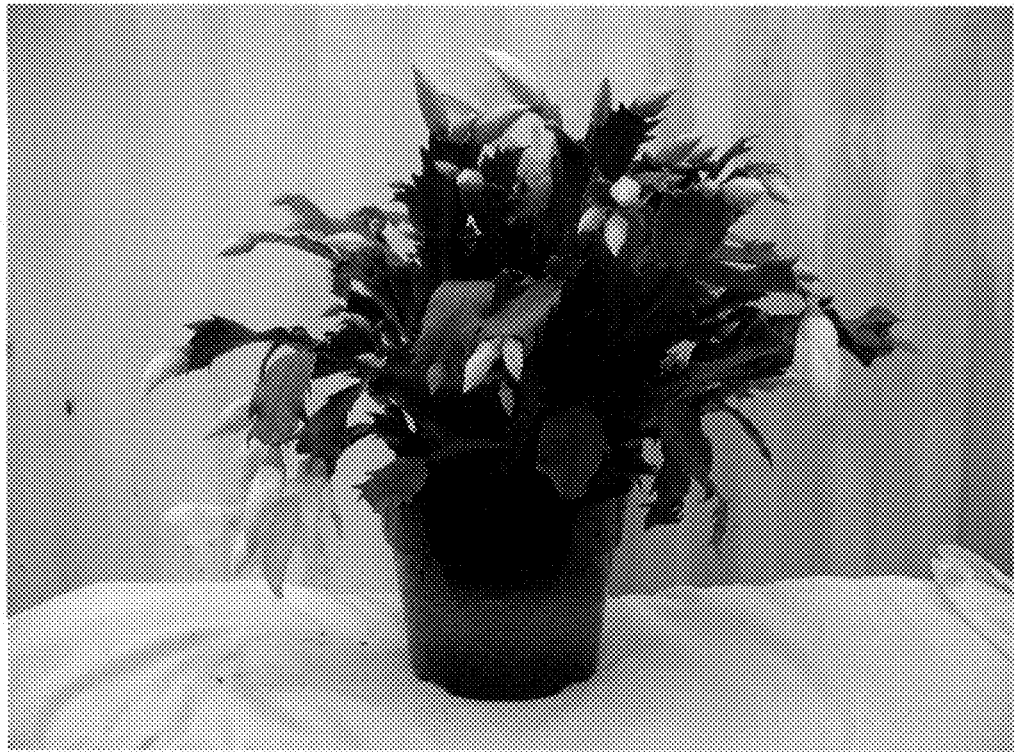
FIG. 1 is a side view of a number of plants grown from a number of cuttings in one pot of the new variety illustrating the overall appearance and form of the plant, and the abundance of blooms.
Figure 2:
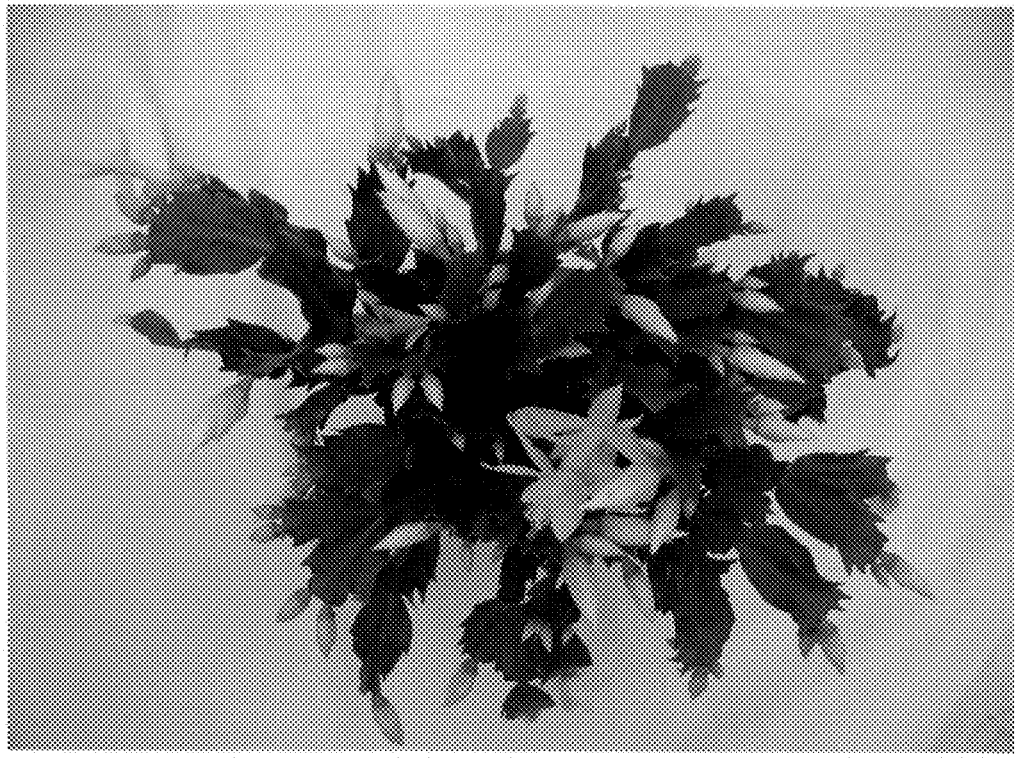
FIG. 2 is a top view of a number plants grown from a number of cuttings in one pot of the new variety, illustrating the overall appearance and form of the plant, and the abundance of blooms.
Figure 3:
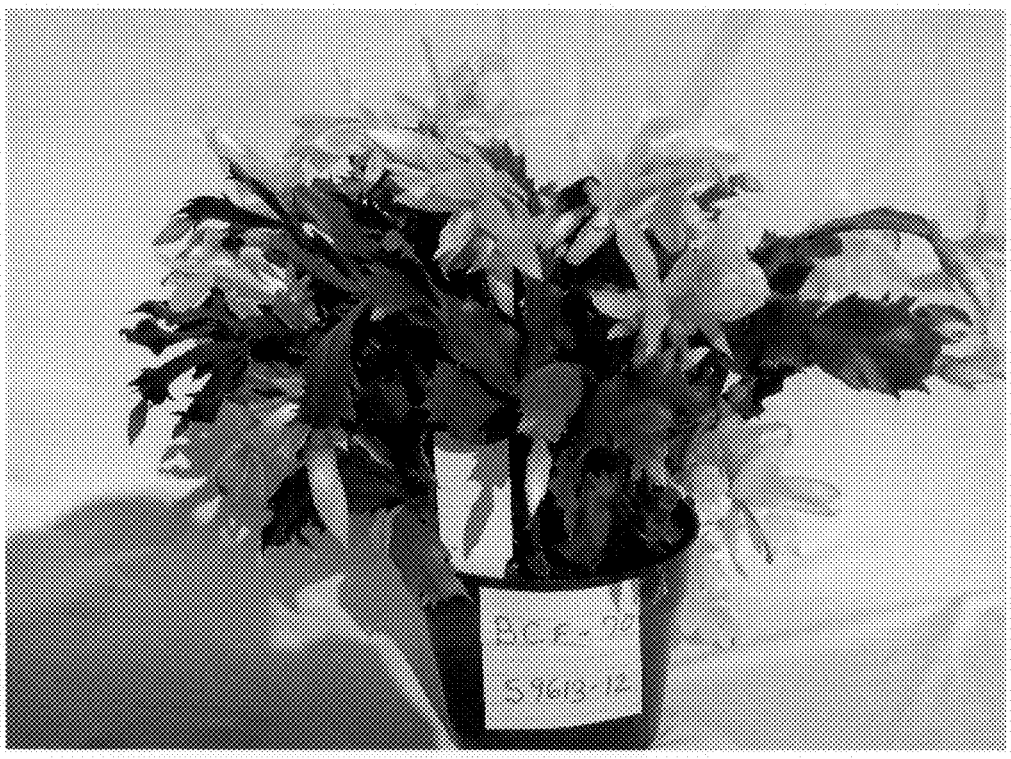
FIG. 3 is a side view of a number plants grown from a number of cuttings in one pot of the new variety, illustrating the overall appearance and form of the plant, and the abundance of blooms.
Figure 6:
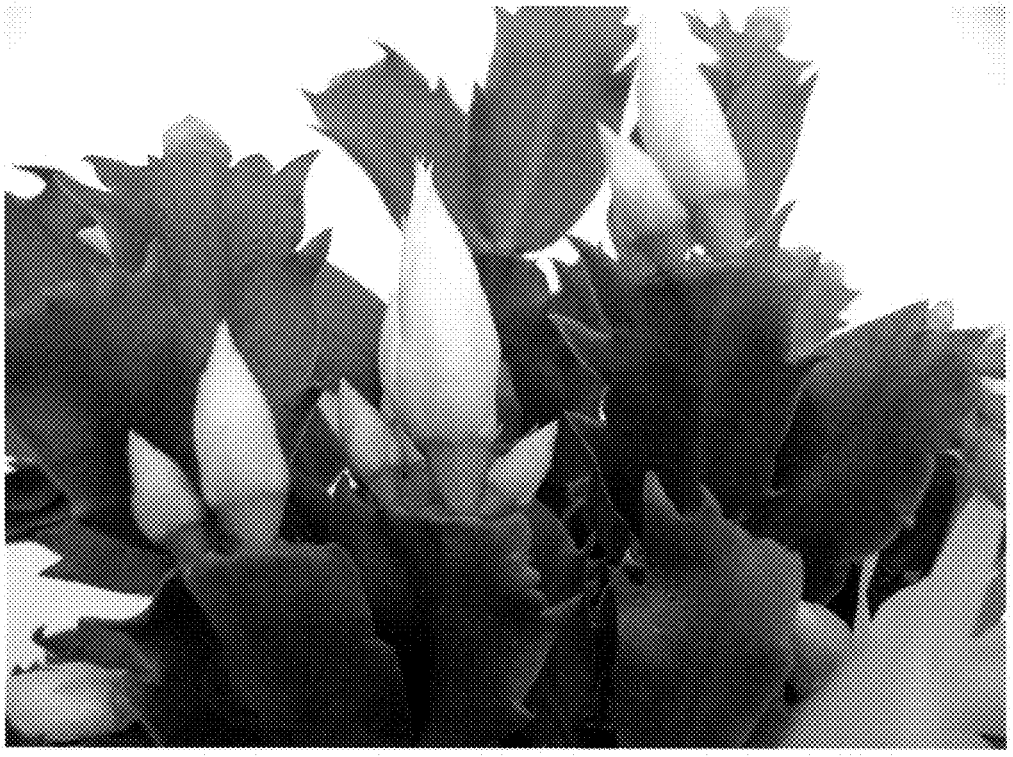
FIG. 6 is a side view of the uppermost phylloclades of a number of plants showing mature buds of the new variety that are close to being ready to open.
Figure 5:
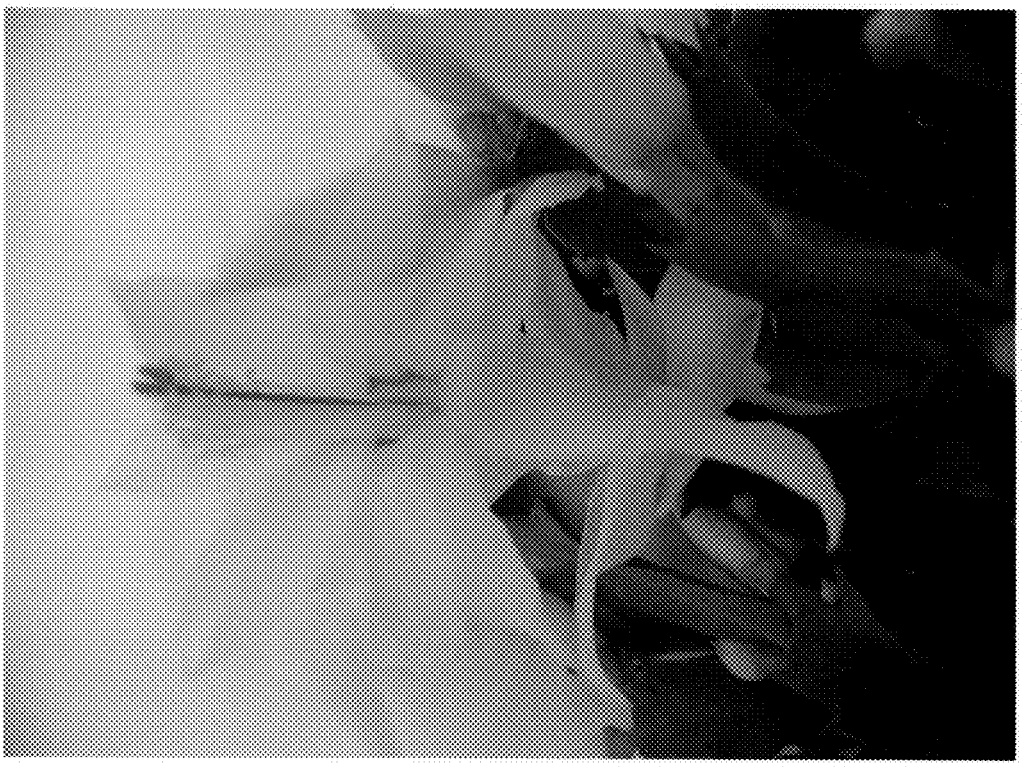
FIG. 5 is a side view of a bloom of the new variety.
Figure 4:
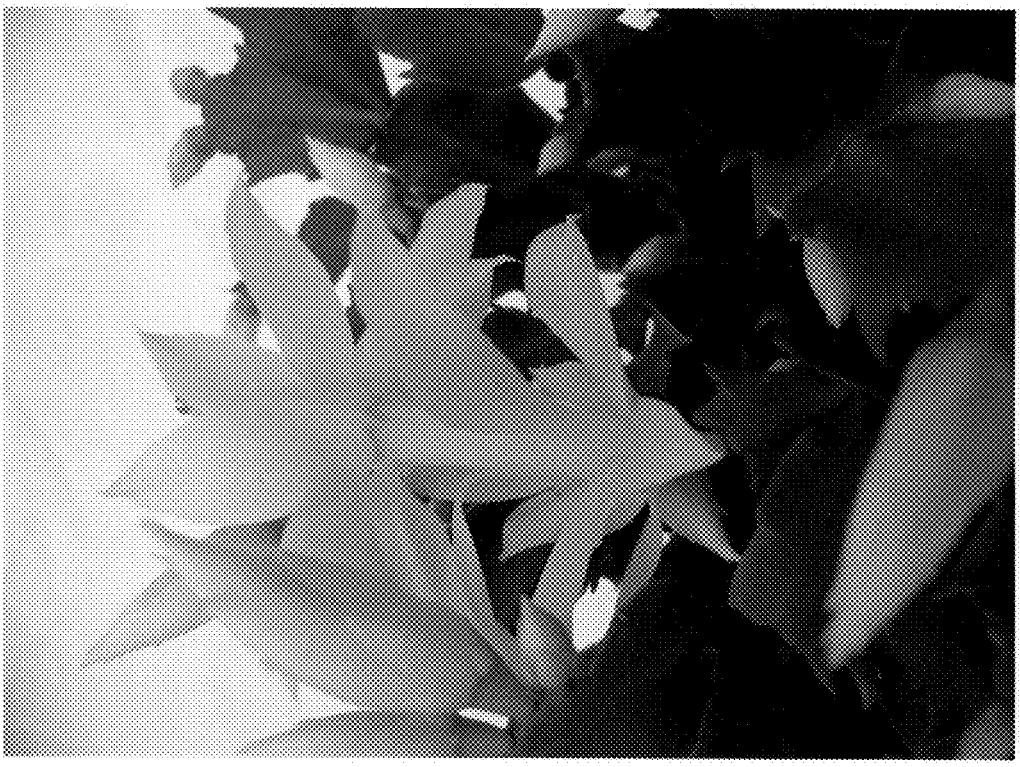
FIG. 4 is a side view of a bloom of the new variety.
Figure 8:
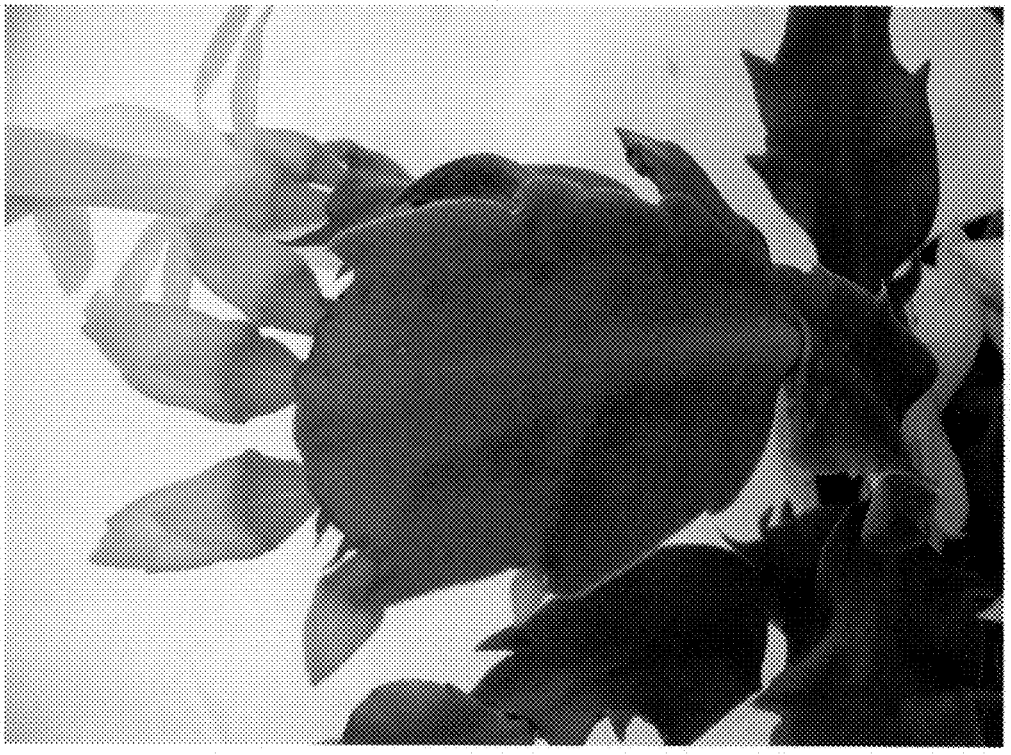
FIG. 8 is a side view of an uppermost phylloclade of the new variety.
Figure 7:
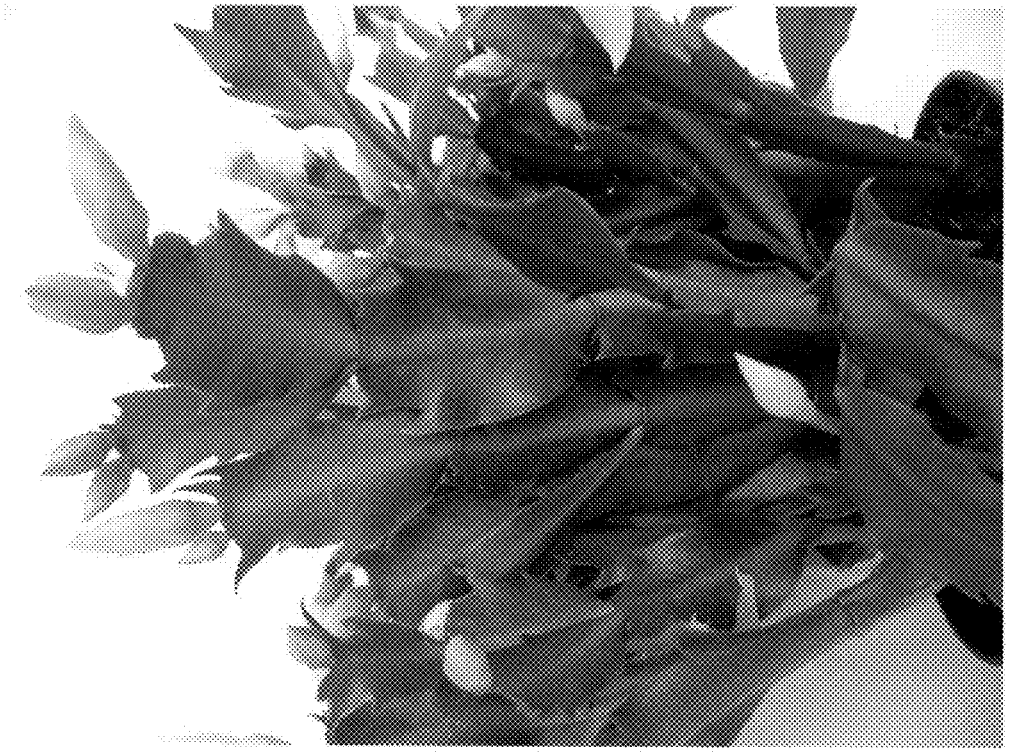
FIG. 7 is a side view of a number plants grown from a number of cuttings in one pot of the new variety, illustrating the overall appearance and form of the plant.

The following is a detailed description of the new variety. The new variety has not been observed under all possible environmental conditions. Color designation and other values stated may deviate slightly from the stated values from flowering to flowering, but the deviations will be within the range expected from varying environmental, seasonal and cultural conditions. Color designations were made according to the R.H.S. Colour Chart published by The Royal Horticultural Society of London, England.

The plants observed were grown in 6 inch pots. The tops of the plants observed were approximately 25 to 30 cm above the soil level. The following description is based on observations of optimally fertilized, mature plants.

DETAILED PLANT DESCRIPTION

Name: *Schlumbergera truncata* 'Gail Glazier'.

Classification: Family—Cactaceae.

*Tribe.*—Rhipsalideae (Cactoideae).

*Genus.*—*Schlumbergera.*

*Species.*—*Schlumbergera truncata* (Haw.) Moran [*Epiphyllum truncatum* Haw.; *Zygocactus truncatus* (Haw.) K. Schum.]. Bailey and Bailey and the staff of the Bailey Hortorium, Hortus Third (1976).

*Commercial.*—Thanksgiving Cactus, Christmas Cactus.

Form: Epiphytic, shade-loving, succulent, leafless plant with jointed and branched stems.

Stems:

*General.*—Irregular with much branching (especially when pinched) of upright, adventitiously rootable, flattened phylloclades that have a prominent midrib (especially in phylloclades at the base of mature plants) and prominently toothed lateral wings. Branching can be encouraged in the plant by pinching the top phylloclade.

Phylloclades:

*General.*—The phylloclades are obovate to oblong, elongated and flattened (particularly when young) and have a transversely elongated, areole bearing, truncated apex. From the transversely elongated apex, the wing margins generally run straight or taper slightly to the basal portions (or they flare outwardly somewhat, especially the uppermost phylloclades, where they then taper and merge through a pointed, basal juncture with the phylloclade therebelow). The margins are also toothed and an axillary areole is associated with each tooth.

*Size.*—Length — Mature phylloclades that are over a year old are usually between 45 mm and 60 mm. Width — Mature phylloclades that are over a year old are usually 23 mm to 35 mm. Thickness — Basal phylloclades with up to three levels of phylloclades above them can be as thick as 1 cm at the midrib. Young phylloclades are as thick as 3 to 4 mm at the center, and tapering to 1 mm near the edges.

*Color.*—Mature phylloclades are predominately R.H.S. 146 A (yellow-green group), young phylloclades are the same.

*Midrib.*—General — Extends longitudinally of phylloclade and continuously through joints with laterally tapering cortex at wing insertions. Pith surrounds the vascular bundles that branch and provide lateral extensions of the vascular system to marginal teeth. Texture — Smooth, waxy epidermis with wax in small embedded scales and becoming corky in basal stem areas with age.

*Wings.*—General shape — Generally flattened from midrib cortex to tooth insertions with slight thinning taper toward margins. Margins — Toothed (modified leaves). Texture — Succulent to leathery with smooth, waxy epidermis having wax arranged in small embedded scales and becoming corky in basal plant areas with age.

*Teeth.*—General shape — Generally flattened and tapering along margins from wing insertion to an apex, having a hyaline, pointed spine with nonpredicatable bending. Adaxial margin shape: Generally concave, so that teeth project generally distally of the phylloclade base in an alternate arrangement, but also with both straight and convex adaxial margin tendencies. Abaxial margin shape: Irregular with tendencies toward straight to convex. Tooth Margins: Entire. Texture — Succulent to leathery with a smooth waxy epidermis having wax in small embedded scales and becoming corky in basal plant areas with age. Number — Usually 2to 4 on each side, mostly 3. Size — Teeth of mature phylloclades are 1 mm thick at insertion point with wings. Areole to apex dimension (adaxial margin side): usually 3 to 8 mm in length.

Areoles:

*Terminal areole.*—Large, compound, elongated, oval-shaped with several acicular bristles, copious multicellular hairs, and several buds that may mature into either new phylloclades or flowers. The opposite ends of the areole are located adjacent to subsidiary areoles which are in turn located at the axils of the uppermost teeth located at the distal end of the of phylloclade.

*Axially areoles.*—Acicular bristles without glochidia but having copious, short, brownish to colorless, multicellular hairs. Areoles are sometimes found in the basal portion of the phylloclade in association with a vestigial tooth that is less than 1 mm in length. (Vestigial teeth not considered in teeth number or length of teeth.)

Buds: Unarmored and ovid, generally R.H.S. 145 B (yellow-green group)).

Flowers:

*General.*—Sessile, zygomorphic, usually in pairs, triplets or solitary, terminal, perfect, and epigynous with double hypanthium and tepals (undifferentiated whorled sepals and petals) having a spiral emergence as a perianth provided with a sepaloid series of free tepals, a tube laminating series of tepals, and a tube forming series of united tepals.

*Sepaloid series of tepals.*—General: Free tepals inserted on top of the ovary. Shape: Deltoid in outer members of the whorl and grading inwardly on the whorl to tepals which are ovate and less frequently elliptical. Tips are broadly acuminate with some acute tendencies, and margins are entire with sparse irregular teeth appearing mainly in the apex areas. Texture: Succulent and glabrous outer whorl members and grading inwardly in the whorl to silken blades with fleshy basal areas. Number: Usually 5. Size (at full bloom): Base-tip dimension — 6 mm to 18 mm. Width dimension — 5 mm to 14 mm. Color: The sepaloid series of tepals are predominantly R.H.S. 155D (white group) and translucent. The outermost and smallest tepals are R.H.S. 145 A (yellow-green group).

*Tube laminating series of tepals.*—General: Tepals inserted on ovary and basally united below the throat as outer laminations on the perianth tube and with progressively greater amounts of basal fusion inwardly in the whorl. Shape: Grading inwardly in the whorl with progressively longer base-tip dimensions and with blade areas changing inwardly from ovate to broadly elliptical and with acute tips. Entire margins with sparse irregular teeth mainly in apex areas. Texture: Succulent, slightly fleshly basal areas with silken blades. Number: usually 6. Size (at full bloom): Base-tip dimension — 18 mm to 42 mm. Width dimension — 15 and 20 mm. Color: The margins and distal ends of the tube laminating series of sepals are R.H.S. 155 D (white group) on both the abaxial and adaxial surfaces.

*Tube forming series of tepals.*—General: Tepals basally united to form a hollow perianth tube that is inserted on ovary and equipped with a irregular carina (keel) at the throat. Shape: Perianth tube — Elongated and ellipsoidal to oval in cross-section. Blades — Generally elliptic to broadly elliptic with ovate tendencies and with acuminate tips. Entire margins with sparse, irregular teeth mainly in apex area. Carina (keel) — Transcending and irregular. Texture: Perianth tube — Thick, succulent, and slightly ribbed. Blades — Translucent and silken. Carina (keel) — Fleshy. Blade number: 8. Size (at full bloom): Base-tip dimension — 65 to 74 mm. Perianth tube — Base to throat length is 37 to 42 mm. Color (at full bloom): Perianth tube — R.H.S 73 D (red-purple group). Blades — The inner interface between the blades of the tube forming tepals and the tube is R.H.S. 74 A (red-purple group). Veins in the perianth tube are R.H.S. 62 C (red-purple group). Orientation at full bloom: The blades of tube forming tepals are reflexed, the tube is angled from the axis of the ovary.

*Androecium* (*stamens*).—General: Numerous exserted and diadelphous stamens with one group having filaments basally fused to the perianth tube and the other group having filaments basally united to form a nectary housing. Filament: General — Translucent and glabrous with anther connective. Shape — Long, slender and gradually tapering from base to anther connective. Texture — Glabrous and silken. Color — Translucent white R.H.S. 155D (white group). Number — approximately 80. Size (at full bloom) — Length: 40 to 65 mm. Anthers: Shape — Rod shaped. Size — 1 mm long. Texture — Course or grainy. Color (pollen color) — R.H.S. 10 C (yellow group).

*Gynoecium* (*pistil*).—General: Compound, parietal placentation with united style surrounded by an annular diffuse nectary at its insertion. Style: General — Stout and inserted in ovary. Shape — Elongated. Texture — Fleshy and glabrous. Color — R.H.S. 61 B (red-purple group) just below stigma, changing to 71 B (red-purple group) at its base. Size (at full bloom) — 65 mm long. Stigma: General — Exserted and erect with anywhere from 4 to 7 inner marginally adhering lobes. Shape — Elongated and tapering toward lobe tips and having relatively blunt apices. Texture —

Fleshy and smooth with short glutinous hairs. Color — R.H.S. 74 A (red-purple group). Size — 4 mm long.

Ovary:

*General.*—Thin epidermis and distally located concavity, and with a single cavity usually having 6 or 7 carpels with numerous ovules.

*Shape.*—Terete to ovoid and generally broadening from insertion to floral end.

*Texture.*—Succulent and glabrous with thin outer epidermis. Size (at full bloom).

*Height.*—10 to 13 mm. Width — 11 mm. Color: 145 A (yellow-green group).

I claim:

1. A new and distinct variety of Cactaceae plant, substantially as herein shown and described.

* * * * *